United States Patent [19]

Campbell

[11] Patent Number: 4,693,893
[45] Date of Patent: Sep. 15, 1987

[54] VACCINES FOR EQUINE INFLUENZA

[75] Inventor: David A. Campbell, Palo Alto, Calif.

[73] Assignee: Burroughs Wellcome, N.C.

[21] Appl. No.: 596,447

[22] Filed: Apr. 3, 1984

Related U.S. Application Data

[63] Continuation-in-part of Ser. No. 565,648, Dec. 27, 1983, abandoned.

[30] Foreign Application Priority Data

Jan. 8, 1983 [GB] United Kingdom ................. 8300467

[51] Int. Cl.$^4$ ................. A61K 39/155; A61K 39/295
[52] U.S. Cl. .................................................. 424/89
[58] Field of Search ........................................ 424/89

[56] References Cited

U.S. PATENT DOCUMENTS

| | | | |
|---|---|---|---|
| 3,518,347 | 6/1970 | Pavilanis et al. | 424/89 |
| 3,869,546 | 3/1975 | Lund I | 424/89 |
| 3,920,811 | 11/1975 | Lund II | 424/89 |
| 4,009,258 | 2/1977 | Kilbourne | 424/89 |
| 4,024,235 | 5/1977 | Weetall et al. | 424/1 |
| 4,206,287 | 6/1980 | Hannoun et al. | 424/89 |
| 4,552,757 | 11/1985 | Murphy et al. | 424/89 |
| 4,552,758 | 11/1985 | Murphy et al. | 424/89 |

FOREIGN PATENT DOCUMENTS

| | | | |
|---|---|---|---|
| 113665 | 7/1984 | European Pat. Off. | 424/89 |
| WO8303546 | 10/1983 | PCT Int'l Appl. | 424/89 |

OTHER PUBLICATIONS

Presslur, C.A. 72#, 136378y(1970) of Tieraer21-6.Umsch. 1969 24(12): 584-7, Horse Influenza Adsorbed Vaccincs.

Rouse et al. I-II, CA. 72#, 98582A, 98583B(1970) of Can. J. Comp. Med 1970 34(1): 1-6, 7-12, Response of ponies to Myxovirus Influenza A-Equi 2.

Nayak, C.A. 76#, 1369832(1972) of J. Gen. Virol. 1972 14pt., 163-67, Depective Virus RNA Synthesis in Chick Embryo cells.

Nayak, GA. 79#, 113165C (1973)of Symp. Ser. Immunobioc. Stand. 1973 20:362-370, E. Quine Influenza RNA Synthesis in Chick Embryo Pibrosyents.

Frerichs et al. GA. 79#, 113745w 1973 of Symp. Ser. Immunobioc. Stand 1973, 20, 338-346, H-1 Test Used in Serocodcac Studies of Equine Influenza.

Laver et al. CA. 78#, 122447g, 1973 of Virology 1973 51(2): 383-391, Origin of Pandemic Influenza #1 III, Evidence Implicating Equine Influenza.

Laver et al., CA. 89#, 195230T, 1928 of Top. Infect. Dis. 1978 3(inf.): 139-144, Equine Influnza Virus Implicated.

Weremowicz., CA. 97#, 116258k (1981), of Zencra Lbl, Verteraermed, 190 27(7) 549-550 Polypedtions of Equine Inpuvenza Virus.

C. Sweet and H. Smith, Pathogenicity of Influenza Virus, *Microbiological Reviews,* 44, #22, #1 Jun. 1980, pp. 303-330.

(List continued on next page.)

*Primary Examiner*—Shep K. Rose
*Attorney, Agent, or Firm*—Don A. L. D. Brown; Gregory D. Williams

[57] ABSTRACT

It is known that the human influenza virus strain A/-Puerto Rico/8/34 grows particularly well in eggs and that reassorted viruses having it as a parent may also grow well in eggs. It has now been found that certain reassortants of A/PR/8/34 and equine influenza viruses, namely those which comprise the RNA7 segment from A/PR/8/34, will grow in cell culture, even though the parent equine influenza vius will not.

Thus the specification describes and claims: reassorted viruses comprising genes for surface antigens of equine influenza viruses and the RNA7 segment from A/PR/8/34; methods of obtaining such viruses by reassortment; methods of propagating such reassorted viruses in cell culture, especially Vero cells; vaccines against equine influenza comprising such reassorted viruses; and methods of vaccinating equines against influenza.

4 Claims, 1 Drawing Figure

OTHER PUBLICATIONS

C. Scholtissek, et al. Correlation of Pathogenicity and Gene Constellation of An Influenza A, *Virology*, S1, 1977, pp. 74–80.

P. Palese and J. L. Schulman, Differences in RNA Patterns of Influenza A viruses, *J. of Virology*, 17, 3, Mar. 1976, pp. 876–884.

M. D. Lubeck, et al., Susceptibility of Influenza A Viruses to Amantadine Is Influenced by the Gene Coding for M Protein, *J. of Virology*, 2, Dec. 1978, pp. 710–716.

W. Rohde, et al. Biochemical Studies on Influenza Viruses, *Virology*, 79, 1977, pp. 393–404.

J. W. Almond, A Single Gene Determines the Host Range of Influenza Virus, *Nature*, 270, Dec. 15, 1977, pp. 617–618.

F. X. Bosch, et al., RNA and Protein Synthesis in a Permissive and an Abortive Influenza Virus Infection, Natl. Inst. for Med. Research, Div. of Virology, Mill Hill, London NW7, pp. 465–473.

VACCINES FOR EQUINE INFLUENZA

This is a continuation in part of U.S. patent application No. 565,648 filed Dec. 27, 1983, now abandoned.

BACKGROUND OF THE INVENTION

The present invention relates to the field of novel genetically reassorted viruses, their use in veterinary medicine, a process for their preparation, vaccines prepared from them and methods of treatment of animals using them.

Equine influenza is a disease of horses of considerable veterinary and commercial significance. It is caused by RNA-containing equine influenza viruses, which belong to the family Orthomyxoviridae. Equine influenza virus, and indeed human influenza virus, each contain a segmented genome (Rohde et al, *Virology* (1977) 79,393–404 and Palese & Schulman, *J. Virol*. (1976) 17, 876–84). Genomic segmentation enables the discrete RNA segments of two parent viruses to reassort or recombine resulting in the production of progeny bearing RNA segments from both parents. Genetically reassorted viruses may be obtained by infection of for example hen eggs with two genetically distinct strains or sub-types of a particular virus, whereby the respective nucleic acid of the two parent viruses recombines to form a genome different from that of either parent but possessing characteristics from each of them.

In consequence of the unavailability of a reliable and effective chemotherapeutic agent to treat equine influenza, it has been customary in recent years to vaccinate horses against the disease. However, there is no cross-immunity between the two serotypes of equine influenza (Eq 1 and Eq 2). As a result of this, and because new strains of each serotype continually emerge and there is variable cross-immunity between all strains of the same serotype, it is desirable to be able readily to produce a vaccine for each of the various strains.

Traditionally, viruses that are used for influenza vaccine production are grown in fertile hen eggs. This technique is, however, costly and labour intensive especially because of the difficulty of purifying the resultant virus particles after they have been in contact with egg protein. Insufficient purification can cause immunogenic reactions in the vaccinated animal.

It has been disclosed (U.S. Pat. No. 4,009,258 (E. D. Kilbourne, Mount Sinai School of Medicine); E. D. Kilbourne, Proc. Nat. Acad. Sci. 75(12) 6258; M. Baez et al, J. Infect Diseases 141(3) 362) that reassorted viruses may be obtained from the human influenza strain A/Puerto Rico/8/34 and other influenza viruses, the said reassortants giving especially high yields when grown in eggs.

BRIEF SUMMARY OF THE INVENTION

It has now surprisingly been found that is an equine influenza virus is genetically reassorted to produce a virus containing certain RNA derived from A/Puerto Rico/8/34, the genetically reassorted virus is able to grow in cell culture. There is no clear correlation between having a high yield in eggs and the ability to grow in cell culture, and there is no teaching in the prior art to suggest that a virus which grows well in eggs is likely to grow in cell culture.

Therefore a first aspect of the present invention provides a genetically reassorted virus derived from an equine influenza virus and the human influenza virus A/Puerto Rico/8/34, which reassorted virus comprises RNA derived from the equine influenza virus coding for at least one surface antigen and an RNA segment derived from A/Puerto Rico/8/34 which codes for matrix protein.

It is to be understood that it is not necessary for one of the parental viruses to be A/PR/8/34, only for the said RNA segment in the reassorted virus to be ultimately derived from A/PR/8/34. Thus A/PR/8/34 could be a "grandparent" or "great-grandparent" etc of the virus in accordance with the invention. It has been established that the said RNA segment which codes for matrix protein is that which is termed RNA 7.

A genetically reassorted virus in accordance with the invention has at least some of the antigenic characteristics of the parent equine influenza virus but is endowed with the ability to grow in certain cell cultures, especially cultures of Ineteroploid monkey cells, for example Vero cells.

Human influenza virus strain A/Puerto Rico/8/34 is deposited with the American Type Culture Collection under accession no. VR 95. Strains of equine influenza virus are available from The Animal Health Trust, Equine Research Station, P.O. Box 5, Balaton Lodge, Snailwell Road, Newmarket, Suffolk CB8 7DW and from WHO Collaborating Centre, Holly Hill, London.

Whereas it has been established by the applicants that the RNA segment which codes for matrix protein enables growth in cell culture to take place, it is not clear as to whether the matrix protein itself confers this ability: it may be some other gene product coded for by the same RNA segment.

The involvement of matrix protein in general in virus growth in cell culture was suggested by Bosch et al, (in Negative Strand Viruses and the Host Cell (1978), Academic Press, edited by B. W. J. Mahy and others, page 465). However, this paper relates to the growth of fowl plague virus (FPV) and no mention is made of equine influenza virus. In view of the well known difficulty in making predictions about the behaviour of one type of influenza virus based on observations of another, this distinction is by no means trivial. See, for example Scholtissek et al, *Virology* (1977) 81 74–80, which illustrates the proposition that apparently small changes between influenza viruses have profound effects. This is amplified by Sweet and Smith (*Microb. Revs.* (1980) 44(22), 303–30). Furthermore, there has been no suggestion that the segment in A/PR/8/34 coding for matrix protein is effective in conferring the ability to grow in cell culture.

In a preferred genetically reassorted virus in accordance with the present invention, the RNA which is derived from the equine influenza virus codes for a haemagglutinin antigen. A further preferred genetically reassorted virus contains, in addition, RNA derived from the equine influenza virus which codes for a neuraminidase surface protein. Suitable strains of equine influenza virus are A/Eq 1/Newmarket/77 and A/Eq 2/Brentwood/79. Other strains of equine influenza virus from which a genetically reassorted virus according to the present invention may be derived include A/Eq 1/Cornell/74, A/Eq 2/Columbus /2/78 and A/Eq 2/Cambridge/80.

A second aspect of the present invention provides a process for the preparation of a genetically reassorted virus in accordance with the first aspect of the invention, which process comprises (a) allowing (i) equine influenza virus (termed herein the equine virus) and (ii)

the human influenza virus strain A/Puerto Rico/8/34 or a virus comprising the RNA 7 segment thereof (termed herein the PR8 virus) to grow under conditions in which genetic reassortment can take place, (b) selecting for genetically reassorted viruses having surface antigens from only the equine influenza virus but other RNA from the human influenza virus strain, and (c) selecting those reassortants from step (b) which will grow in cell culture.

Preferred growth conditions involve simultaneous infection of hen eggs with both viruses and incubation for 24 to 48 (preferably 36) hours at 37° C. Genetically reassorted viruses can subsequently be selected by antibody pressure and susceptibility to an antiviral agent that acts specifically against equine influenza viruses, such as amantadine and rimantadine. Thus the viruses can be incubated and grown in the presence of antibody to both surface antigens of the PR8 virus parent. Such antibodies suppress the growth of the PR8 virus parent and genetically reassorted viruses bearing the PR8 virus surface antigens. At the same stage the viruses may be grown in the presence of for example amantadine, to which all known equine influenza viruses are sensitive, and to which A/Puerto Rico/8/8/34 is resistant. The only viruses which can grow under the combination of these conditions will be genetically reassorted viruses which do not bear surface antigens from A/PR/8/34 but which comprise the genetic segment (namely RNA 7) from A/PR/8/34 which confers amantadine resistance and which has replaced the genetic segment from equine influenza virus which confers amantadine sensitivity. See Lubeck et al, *J. Virol* (1978) 28 (3) 710–16.

The antigenic identity of genetically reassorted viruses thus produced can then be determined, for example by haemagglutination-inhibition and neuraminidase-inhibition assays to establish the type of equine influenza antigens on the resultant viruses. Genetically reassorted viruses with desired surface antigens are then be tested for their ability to grow in, for example, Vero cells, and further adapted to the cells by serial passage, for example six times.

A genetically reassorted virus in accordance with the first aspect of the present invention can be grown in cell cultures, for example Vero cells, preferably with the addition of trypsin. Growth would suitably be allowed to take place for 2 to 5 days at 37° C. in the presence of from 0.1 to 20 μg/ml, preferably 2.5 μg/ml trypsin. A greater concentration of trypsin can be used if it has been partially inactivated by gamma-irradiation sterilisation. Subsequently, harvested virus can then be attenuated by serial passage or inactivated before incorporation into a vaccine. Inactivation may be achieved by formalin (at a concentration of from 1 part in 500 to 1 part in 3000, preferably 1 part in 1000 to 1 part in 2000 of a 40% w/w aqueous stock solution) or acetylethyleneimine or ethyleneimine or beta-propiolactone.

A third aspect of the present invention provides a vaccine comprising inactivated or attenuated genetically reassorted virus in accordance with the first aspect of the present invention or obtained by a method in accordance with the second aspect of the invention in association with a veterinarily acceptable carrier. For broader protection the vaccine preferably comprises two genetically reassorted viruses derived from different parent strains of equine influenza virus, i.e. one genetically reassorted virus derived from a serotype 1 equine influenza virus and a second one derived from a serotype 2 equine influenza virus. In addition a third element may be added to the vaccine such as tetanus toxoid.

Veterinarily acceptable carriers, in this instance, are liquid media suitable for use as vehicles to introduce the virus particles into the animals. Examples of such a carrier are saline solution and phosphate buffered saline.

Where the vaccine comprises inactivated genetically reassorted virus(es) an adjuvant may be added for stimulating the immune response and thereby enhancing the effect of the vaccine. Convenient adjuvants for use in the present invention include Freund's complete adjuvant and, more particularly, saponin, *Corynebacterium parvum* (Coparvax), aluminium phosphate and aluminium hydroxide or a mixture of these or other known adjuvants. (The word "Coparvax" is a Trade Mark). Alternatively the vaccine may be formulated into an oil-in-water emulsion using oils such as Marcol and/or Arlacel.

Conveniently the vaccines may be so formulated as to contain a final concentration of a single genetically reassorted virus in the range of from 1 to 50, preferably 2 to 15, most preferably 10, μg/dose. After formulation the vaccine may be incorporated into a sterile container which is then sealed and stored at a low temperature, for example 4° C., or may be freeze dried.

In order to induce immunity in horses to equine influenza one or more doses of the vaccine, formulated as described above, may be administered. It is recommended that each dose is 0.5 to 5 ml, preferably 1 to 3 ml, most preferably 2 ml of vaccine.

When the vaccine contains two genetically reassorted viruses derived from serotype 1 and serotype 2 equine influenza virus respectively, the concentration for each virus is in the range of from 1 to 50, preferably 2 to 15, most preferably 10, μg/dose. Each dose is 0.5 to 5 ml, preferably 1 to 3 ml, most preferably 2 ml of vaccine.

A fourth aspect of the present invention provides a method of immunising horses against influenza, which method comprises administering to a horse a non-toxic, effective immunising amount of a vaccine in accordance with the third aspect of the present invention.

A vaccine of the present invention is desirably administered by subcutaneous or intramuscular injection. The treatment may consist of a single dose of vaccine or a plurality of doses over a period of time. An advantageous treatment schedule requires administration of two doses of vaccine with an interval of 3 to 7, preferably 4 to 6, weeks between doses. If longer protection is required, booster doses may be administered after longer intervals, for instance after 6 months or annually.

DETAILED DESCRIPTION OF EMBODIMENTS OF THE INVENTION

Figure 1:
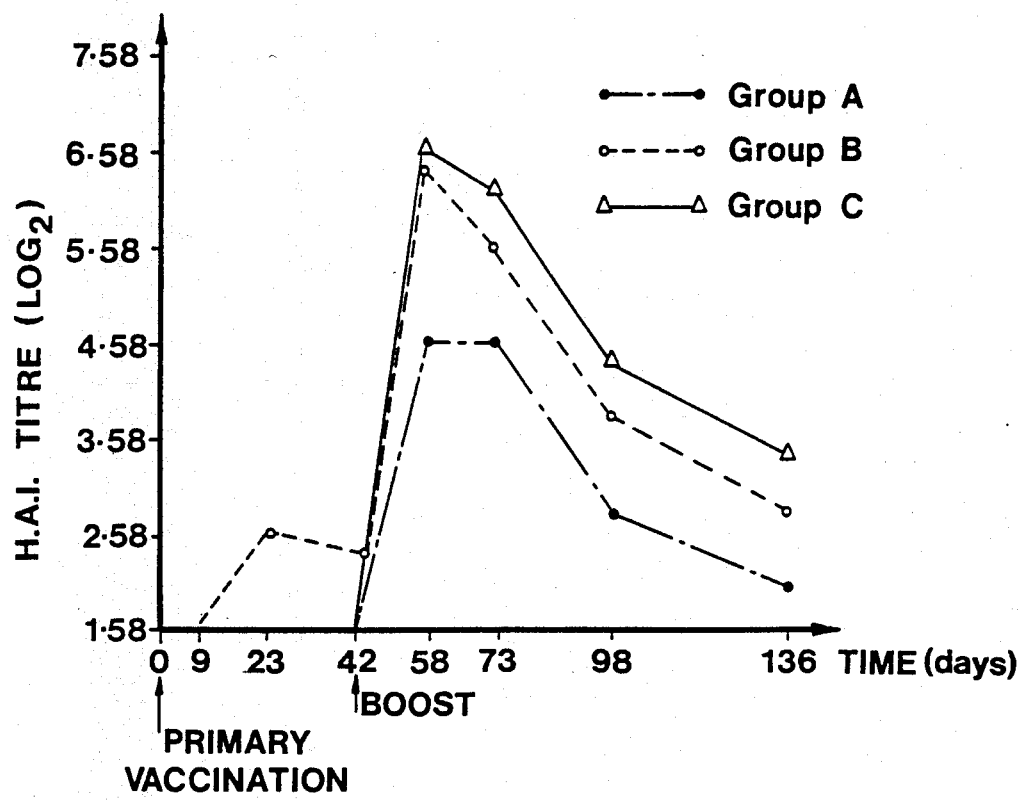
FIG. 1 is a graph of the serological response of a sample of horses to a vaccine of the invention, as is explained more fully in Example 6.

The following Examples serve to illustrate the invention but are not intended to limit it in any way.

EXAMPLE 1

Preparation of a genetically reassorted virus derived from A/Eq 2/Brentwood/79 and A/Puerto Rico/8/34.

(a) Cloning of parent viruses

Parent virus stocks were cloned three times at limit dilution in fertile specific pathogen free (SPF) hen eggs. (Limit dilution is the highest dilution of virus that will produce a positive result on the system in which it is cultured). Serial 10-fold dilutions of virus were made in phosphate buffered saline (PBS) and 10% tryptose phosphate broth (TPB) (virus diluent) and 0.1 ml of each dilution was subsequently inoculated into ten 10 day old SPF eggs and incubated for 48 hours. After chilling, the eggs were tested for haemagglutinating activity (see below) and allantoic fluid from one egg at the limiting dilution was taken for further cloning. The allontoic fluid from the A/Puerto Rico/8/34 containing egg was taken and passed once at $10^{-4}$ dilution to increase the volume available.

Limit dilution factors for the two viruses are shown in Table 1, which follows.

TABLE 1

Limit dilution factors for A/Eq 2/Brentwood/7(2B79) and A/Puerto Rico/8/34 (PR8) in SPF eggs.

| | Limit Dilution | |
|---|---|---|
| | PR8 | 2B79 |
| Cloning 1 | $10^{-9}$ | $10^{-7}$ |
| Cloning 2 | $10^{-10}$ | $10^{-6}$ |
| Cloning 3 | $10^{-10}$ | $10^{-6}$ |
| Pass | $10^{-4}$ | ND |

ND = not done

Separate portions of allantoic fluid containing A/Puerto Rico/8/34 and A/Eq 2/Brentwood/79 were stored at $-70°$ C. until use.

(b) Reassortment

Six eggs were inoculated with 0.1 ml of a 10-fold dilution of A/Eq 2/Brentwood/79 that had been obtained by the triple cloning in step (a) above. Two of these eggs were also inoculated with 0.1 ml of a 10,000-fold dilution of the triple cloned A/Puerto Rico/8/34; a further two were inoculated with 0.1 ml of a 1,000-fold dilution of A/Puerto Rico/8/34 and the last two eggs were inoculated with 0.1 ml of a 100-fold dilution of A/Puerto Rico/8/34. The six eggs were then incubated at 37° C. for 24 hours. Allantoic fluids from each pair of eggs were harvested and pooled.

To 200 $\mu$l of each pool was added 20 $\mu$l of anti-A/Puerto Rico/8/34 antiserum. The fluid and serum were incubated overnight at 4° C. 25 $\mu$l amantadine at 5 mg/ml was then added. 100 $\mu$l of the resulting mixture was inoculated into each of a pair of eggs, which were subsequently incubated for 36 hours at 37° C. Fluid from these eggs was harvested and pooled and subsequently diluted in a 1,000-fold dilution of A/Puerto Rico/8/34 antiserum and 50 $\mu$g/ml amantadine (final concentration) to give 8 serial dilutions. These were inoculated into eggs (0.1 ml per egg), which were incubated for 48 hours at 37° C. From one egg containing a $10^{-7}$ dilution of virus, allantoic fluid was taken and subjected twice to limit dilution in allantois on shell (Fazekas et al, J. Hyg. (1958) 56, 151). The resulting fluid (about 0.4 ml) was passed once in eggs to yield viruses which were likely to be reassortants because they had survived treatment with A/PR/8/34 antiserum and amantadine.

However, to confirm genetic reassortment, haemagglutination inhibition and neuraminidase inhibition tests were carried out on the putative genetically reassorted viruses.

(c) Haemagglutination inhibition test

Haemagglutination inhibition was determined by the method described in WHO Tech. Rep. No. 170, 1959. Table 2 shows the extent of inhibition of haemagglutination by both parent and genetically reassorted viruses in the presence of antiserum to A/Puerto Rico/8/34 and A/Eq 2/Miami/63, which, like A/Eq 2/Brentwood/79 belongs to the second type of equine influenza virus.

TABLE 2

| | Haemagglutination inhibition test | |
|---|---|---|
| | Antiserum | |
| Virus | A/Puerto Rico/8/34 | A/Eq 2/Miami/63 |
| A/Puerto Rico/8/34 | 5120 | less than 10 |
| A/Eq 2/Brentwood/79 | less than 10 | 160 |
| Genetically reassorted virus | less than 10 | 1280 |

These results clearly show that the genetically reassorted virus has the haemagglutinin antigenic character of the parent A/Eq 2/Brentwood/79 rather than A/Puerto Rico/8/34.

(d) Neuraminidase inhibition test

The neuraminidase inhibition test was carried out by the method recommended by WHO and described by Aymard-Henry et al (Bull. WHO (1973) 48 199–202). The extent of inhibition by both parent and genetically reassorted viruses was again seen in the presence of antiserum to A/Puerto Rico/8/34 and antiserum to A/Eq 2/Miami/63. The results, shown in Table 3, show the inhibition expressed as a percentage of that observed in the presence of normal rabbit serum.

TABLE 3

| | Neuraminidase inhibition test | |
|---|---|---|
| | Antiserum | |
| Virus | A/Puetro Rico 8/34 | A/Eq 2/Miami/63 |
| A/Puerto Rico/8/34 | 78.5 | 30.0 |
| A/Eq 2/Brentwood/79 | 37.9 | 68.1 |
| Genetically reassorted virus | 41.3 | 68.3 |

These results clearly show that the genetically reassorted virus has the neuraminidase antigenic character of the parent A/Eq 2/Brentwood/79 rather than A/Puerto Rico/8/34.

(e) Adaptation of genetically reassorted virus to cell culture

The genetically reassorted virus was adapted to grow in Vero cells (obtainable from Flow laboratories, Irvine, Scotland) by serial passage. This was done at low dilution of inoculum for the early passages, with the dilution being increased as the virus adapted. Table 4 shows the haemagglutinin titres during passage, haemagglutinin titre being a measure of growth.

TABLE 4

Serial Passaging of A/Puerto Rico/8/34 A/Eq 2/Brentwood/79 genetically reassorted virus through Vero cells in the presence of gamma-irradiated trypsin.

| Passage | Inoculation Dilution | Trypsin ($\mu$g/ml) | Haemagglutinin Titre |
|---|---|---|---|
| 1 | Neat | 5 | 32 |
| 2 | Neat | 20 | 4 |
| 3 | $10^{-1}$ | 20 | 64 |
| 4 | $10^{-4}$ | 20 | 32 |
| 5 | $10^{-7}$ | 20 | 96 |
| 6 | $10^{-6}$ | 20 | 256 |

TABLE 4-continued

Serial Passaging of A/Puerto Rico/8/34 A/Eq 2/Brentwood/79 genetically reassorted virus through Vero cells in the presence of gamma-irradiated trypsin.

| Passage | Inoculation Dilution | Trypsin (µg/ml) | Haemagglutinin Titre |
|---|---|---|---|
| 7 | $10^{-6}$ | 15 | 256 |

By current opinion a haemagglutinin titre of 256 is acceptable.

EXAMPLE 2

Preparation of a genetically reassorted virus derived from A/Eq 1/Newmarket/77.

(a) Cloning of parent viruses

Following the procedure outlined in Example 1, parent viruses were triple cloned at limit dilution in SPF eggs. Again, the allantoic fluid from the A/Puerto Rico/8/34 egg was taken and passed once at $10^{-4}$ dilution to increase the volume available. Allantoic fluid was stored at $-70°$ C. until use.

(b) Reassortment

Two eggs were each inoculated with 0.1 ml of a 10-fold dilution of A/Eq 1/Newmarket/77 and 0.1 ml of a 10,000-fold dilution of A/Puerto Rico/8/34. The eggs were incubated at 37° C. for 24 hours and the allantoic fluids were harvested and then pooled. To 200 µl of pooled fluid were added 20 µl of anti-A/Puerto Rico/8/34 antiserum and the resulting mixture was incubated at 20° C. for 4 hours. 0.1 ml of a 10-fold dilution of the resulting allantoic fluid was inoculated into each of three eggs. 250 µg amantadine per egg was also inoculated. The eggs were incubated for 20 hours at 37° C. The resulting allantoic fluid was pooled, 300 µl were taken and 30 µl of anti-A/Puerto Rico/8/34 antiserum was added. 150 µl amantadine (5 mg/ml) was added and 0.1 ml of the mixture was inoculated into each of three eggs, which were incubated at 37° C. for 48 hours. As in Example 1, resultant allantoic fluid was passed at limit dilution 3 times in allantois on shell. A $10^{-4}$ dilution was then prepared and passed into eggs.

(c) Haemagglutinin inhibition test

A haemagglutination inhibition test was then carried out. This test, the results of which are shown in Table 5, showed that the genetically reassorted virus has the haemagglutinin antigenic character of A/Eq 1/Newmarket/79 both in the presence of anti-A/Puerto Rico/8/34 antiserum and anti-A/Eq 1/Prague/56 antiserum. The Prague strain, like the Newmarket strain, is a strain of the first type of equine influenza virus.

TABLE 5

| | Haemagglutination inhibition test | |
|---|---|---|
| | Antiserum | |
| Virus | A/Puerto Rico/8/34 | A/Eq 1/Prague/56 |
| A/Puerto Rico/8/34 | 6144 | less than 12 |
| A/Eq 1/Newmarket/79 | less than 12 | 12288 |
| Genetically reassorted virus | less than 12 | 3072 |

(d) Neuraminidase inhibition test

A neuraminidase inhibition test was also carried out, as for Example 1 except that the antiserum of A/Eq 1/Prague/56 was again used in place of the antiserum to A/Eq 2/Miami/63. The results, shown in Table 6, show that the genetically reassorted virus has the neuraminidase antigenic character of A/Eq 1/Newmarket/79, rather than A/Puerto Rico/8/34. As in Table 3, the figures given are percentage inhibition compared to that observed in the presence of normal rabbit serum.

TABLE 6

| | Neuraminidase inhibition test | |
|---|---|---|
| | Antiserum | |
| Virus | A/Puetro Rico/8/34 | A/Eq 1/Prague/56 |
| A/Puerto Rico/8/34 | 76.5 | 7.8 |
| A/Eq 1/Newmarket/79 | 8.7 | 30.4 |
| Genetically reassorted virus | 15.7 | 58.6 |

(e) Adaption of genetically reassorted virus to cell culture

To improve the growth properties of the genetically reassorted virus in Vero cells, the virus was passaged 7 times under progressive serial dilution in the presence of gamma-irradiated trypsin. The haemagglutinin titre was again measured to monitor growth. The progress of this passaging is shown in Table 7.

TABLE 7

Serial Passaging of A/Puerto Rico/8/34 1/Newmarker/79 genetically reassorted virus through Vero cells in the presence of gamma-irradiated trypsin.

| Passage | Inoculation Dilution | Trypsin (µg/ml) | Haemagglutinin Titre |
|---|---|---|---|
| 1 | Neat | 15 | 32 |
| 2 | $10^{-1}$ | 20 | 1 |
| 3 | $10^{-1}$ | 20 | 32 |
| 4 | $10^{-3}$ | 20 | 32 |
| 5 | $10^{-5}$ | 15 | 48 |
| 6 | $10^{-7}$ | 15 | 64 |
| 7 | $10^{-6}$ | 15 | 96 |

The maximum titre of 96 was judged to be acceptable.

EXAMPLE 3

Using similar methods of those described in Examples 1 and 2 above, reassorted viruses obtained from A/PR/8/34 and, respectively, A/Eq.2/Cambridge/80 and A/Eq.2/Columbus/2/78 were prepared and shown to grow in Vero cells.

EXAMPLE 4

Demonstration that growth in Vero cells is dependent upon the RNA 7 segment of A/PR/8/34

Many different reassorted viruses having genes derived from A/PR/8/34 and from equine influenza viruses were prepared as described above, and tested for growth in Vero cells. A/PR/8/34 and each of the equine parents were also tested for growth. In addition, the source of the RNA of each reassortant was identified by extracting the virion RNA (Hay et al, Virology 83, 337, (1977)) and analysing it by polyacrylamide gel electrophoresis (Palese and Schulman, Proc. Nat. Acad. Sci. 73, 2142, (1976)). The results, given in Table 8, show that growth in the cell culture occurs only when the RNA 7 gene of the virus is derived from A/PR/8/34.

TABLE 8

| RNA segment | Reassortant: 1 | 2 | 3 | 4 | 5 | 6 | 7 | 8 | 9 | 10 | 11 | 12 | A/PR/8/34 | Equine |
|---|---|---|---|---|---|---|---|---|---|---|---|---|---|---|
| P1 | E | E | E | P | P | P | P | E | E | E | E | P | P | E |
| P2 | E | E | E | P | E | P | P | E | E | E | E | P | P | E |
| P3 | E | E | E | P | P | P | P | E | E | E | E | P | P | E |
| HA | E | E | E | E | E | E | E | E | E | E | E | E | P | E |
| NP | E | E | E | P | E | P | P | E | E | E | E | P | P | E |
| NA | E | E | E | E | E | P | P | E | P | P | P | P | P | E |
| M(7) | P | P | P | P | P | P | P | E | E | E | P | P | E | |
| NS | E | E | E | P | E | P | P | E | E | E | E | P | P | E |
| Growth in Vero cells? | + | + | + | + | + | + | + | + | − | − | − | + | + | − |

Notes:
(a) The equine parent for reassortants 1, 2, 3 and 4 was A/Eq. 1/Cornell/74; for 5 it was A/Eq. 1/Newmarket/77; for 6 and 7 it was A/Eq. 2/Columbus/78; for 8, 9, 10 and 11 it was A/Eq. 2/Brentwood/79; and for 12 it was A/Eq. 2/Cambridge/80.
(b) "E" means the segment was derived from the equine parent, "P" from the A/PR/8/34.

EXAMPLE 5

Vaccine Formulation

| | |
|---|---|
| Inactivated genetically reassorted virus derived from A/Eq 1/Newmarket/77 as prepared according to Example 2 | 10 μg |
| Inactivated genetically reassorted virus derived from A/Eq 2/Brentwood/79 as prepared according to Example 1 | 10 μg |
| LF international units immuno purified tetanus toxoid | 200 |
| aluminium phosphate | 10 mg |
| thiomersal | 200 μg |
| Phosphate buffered saline (pH 7.2) to give total volume of | 2 ml. |

EXAMPLE 6

Demonstration of serological response and protection against viral challenge by vaccine.

Twelve Welsh Mountain ponies were vaccinated with a dose of vaccine in accordance with the invention and revaccinated with the same respective dose 21 weeks later. Eight control ponies were not vaccinated. Some vaccine preparations also contained anti-tetanus vaccine. Seven weeks later, haemagglutinin inhibition assays (HIA) were carried out using the vaccine strain Equi 2 virus and then all the ponies were challenged with virulent Equi 2/Newmarket/79 virus, given intranasally. 7 days after the challenge, the ponies were examined for clinical signs of influenza infection (temperature (T) of above 102° F. (38.8° C.) or cough (C)). A post-challenge HAI was carried out 31 weeks after the primary vaccination.

The results, given in Table 9 and FIG. 1, shows that the vaccine gave a dose-related serological response and a good measure of protection against subsequent infection.

TABLE 9

| Group | pony code no. | Treatment | HAI Titres 28 weeks | HAI Titres 31 weeks | Seroconversion | Clinical signs |
|---|---|---|---|---|---|---|
| A | 27 | Dose level 1 + | 192 | 384 | − | |
| | 30 | tetanus | 768 | 768 | − | C |
| | 43 | | 192 | 768 | + | |
| B | 34 | Dose level 3 + | 768 | 1536 | − | |
| | 35 | tetanus | 768. | 768 | − | |
| | 46 | | 48 | 384 | + | |
| C | 22 | Dose level 9 + | 384 | 768 | − | |
| | 28 | tetanus | 192 | 384 | − | |
| | 50 | | 192 | 1536 | + | C |
| D | 15 | Dose level 3 | 192 | 192 | − | C |
| | 18 | without tetanus | 192 | 768 | + | |
| | 21 | | 384 | 768 | − | |
| Controls | 11 | no | 6 | 192 | + | C |
| | 24 | treatment | 6 | 48 | + | TC |
| | 51 | | 6 | 96 | + | TC |
| | 52 | | 6 | 96 | + | C |
| | 53 | | 6 | 96 | + | TC |
| | 54 | | 6 | 384 | + | TC |
| | 55 | | 6 | 96 | + | TC |
| | 56 | | 6 | 96 | + | TC |

N.B. The dose levels are expressed as arbitrary units.

EXAMPLE 7

Growth of reassortants in MDCK Cells.

Following substantially the same procedure as given above in Examples 1 and 2, reassortants of the equine influenza viruses A/Eq1/Newmarket/77 and A/Eq2/-Brentwood/79 with A/PR/8/34 were prepared. The reassortants and the equine parents were each tested twice separately for growth in the Madin-Darby Canine Kidney cell line (MDCK) (available from Flow Laboratories, Irvine, Scotland). As in the case of Examples 1 and 2 above, suitable cell culture conditions for the particular cell line were chosen by reference to published criteria and/or information available from the suppliers of the cell line. The results are presented in Table 10.

TABLE 10

| Inoculum Dilution | HA titre at 3 days | | | |
| --- | --- | --- | --- | --- |
| | Virus 1 | Virus 2 | Virus 3 | Virus 4 |
| neat | 48,24 | 48,32 | <2,32 | not done |
| $10^{-1}$ | <2,<2 | 32,32 | <2,<2 | 192,192 |
| $10^{-2}$ | <2,<2 | 48,48 | <2,<2 | 192,192 |
| $10^{-3}$ | <2,<2 | 48,48 | <2,<2 | 192,192 |
| $10^{-4}$ | <2,<2 | 32,24 | <2,<2 | 192,192 |
| $10^{-5}$ | not done | not done | not done | 128,192 |

Notes
(a) Virus 1 was A/Eq. 1/Newmarket/77
Virus 2 was a reassortant of Virus 1 and A/PR/8/34
Virus 3 was A/Eq 2/Brentwood/79
Virus 4 was a reassortant of Virus 3 and A/PR/8/34
(b) the MDCK cell culture contained 2 μg/ml of trypsin.

What we claim is:

1. A vaccine for either or both of Eq 1 and Eq 2 equine influenza comprising an effective vaccination amount of inactivated genetically reassorted virus grown in cell culture and derived from either or both of an equine Eq 1 and Eq 2 influenza virus and the human influenza virus A/Puerto Rico/8/34 which reassorted virus comprises RNA derived from either or both of Eq 1 and Eq 2 equine influenza virus coding for at least one neuraminidase or haemagglutinin surface antigen and an RNA segment derived from A/Puerto Rico/8/34 which codes for matrix protein in association with a veterinary acceptable carrier which can contain an adjuvant suitable for use as a vehicle to introduce the inactivated virus by parenteral administration into the animal.

2. A vaccine according to claim 1 comprising a plurality of reassorted viruses, some of the viruses being antigenitically distinct from each other.

3. A vaccine according to claim 2 comprising two viruses, one having at least one surface antigen of serotype 1 equine influenza virus and the other having at least one surface antigen of serotype 2 equine influenza virus.

4. A method of vaccinating a horse against either or both of an Eq 1 virus and Eq 2 virus influenza by parenteral administration to the horse of an effective amount of (a) one, or (b) a primary followed by a secondary dosage with an interval of about 3 to about 7 weeks between doses of a genetically reassorted virus derived from either or both of serotype 1 and serotype 2 equine influenza virus, inactivated and formulated with a veternary acceptable carrier which can contain an adjuvant as a vaccine according to claim 1.

* * * * *